US008946160B2

(12) United States Patent
Farber

(10) Patent No.: US 8,946,160 B2
(45) Date of Patent: Feb. 3, 2015

(54) NITRIC OXIDE AMINO ACID ESTERS FOR IMPROVING VASCULAR CIRCULATION, AND PROPHYLAXIS OR TREATMENT OF A CONDITION ASSOCIATED WITH IMPAIRED BLOOD CIRCULATION

(75) Inventor: Michael Farber, Montreal (CA)

(73) Assignee: Oral Delivery Technology Ltd., Montreal, Quebec (CA)

( * ) Notice: Subject to any disclaimer, the term of this patent is extended or adjusted under 35 U.S.C. 154(b) by 0 days.

(21) Appl. No.: 13/881,867

(22) PCT Filed: Oct. 26, 2011

(86) PCT No.: PCT/CA2011/001169
§ 371 (c)(1),
(2), (4) Date: Jul. 15, 2013

(87) PCT Pub. No.: WO2012/079146
PCT Pub. Date: Jun. 21, 2012

(65) Prior Publication Data
US 2013/0287866 A1  Oct. 31, 2013

Related U.S. Application Data

(60) Provisional application No. 61/406,997, filed on Oct. 26, 2010, provisional application No. 61/406,998, filed on Oct. 26, 2010.

(51) Int. Cl.
*A61K 38/00* (2006.01)
*A61P 9/00* (2006.01)
*C07C 229/12* (2006.01)
*C07C 229/22* (2006.01)
*A61K 45/06* (2006.01)
*A61K 31/223* (2006.01)

(52) U.S. Cl.
CPC ............. *A61K 31/223* (2013.01); *C07C 229/12* (2013.01); *C07C 229/22* (2013.01); *A61K 45/06* (2013.01)
USPC ........................................................ 514/13.5

(58) Field of Classification Search
None
See application file for complete search history.

(56) References Cited

U.S. PATENT DOCUMENTS

| | | | | |
|---|---|---|---|---|
| 7,807,716 | B2* | 10/2010 | Farber | 514/551 |
| 2010/0076043 | A1* | 3/2010 | Farber | 514/399 |
| 2010/0311780 | A1* | 12/2010 | Farber | 514/280 |
| 2011/0195935 | A1* | 8/2011 | Farber | 514/91 |

FOREIGN PATENT DOCUMENTS

WO   WO2010034118   *  3/2010

* cited by examiner

*Primary Examiner* — Maury Audet
(74) *Attorney, Agent, or Firm* — Klauber & Jackson LLC

(57) ABSTRACT

Use of nitric oxide amino acid esters for improving vascular circulation, and prophylaxis or treatment of a condition associated with impaired blood circulation, such as peripheral vascular disease. The nitric oxide amino acid esters may be co-administered with an antimicrobial in topical or transdermal compositions for improving vascular circulation, and prophylaxis or treatment of a condition associated with impaired blood circulation.

3 Claims, No Drawings

NITRIC OXIDE AMINO ACID ESTERS FOR IMPROVING VASCULAR CIRCULATION, AND PROPHYLAXIS OR TREATMENT OF A CONDITION ASSOCIATED WITH IMPAIRED BLOOD CIRCULATION

CROSS REFERENCE TO RELATED APPLICATIONS

The present application is a National Stage Application claiming the priority of co-pending PCT Application No. PCT/CA2011/001169 filed Oct. 26, 2011, which in turn, claims priority from U.S. Provisional applications Ser. No. 61/406,997 filed Oct. 26, 2010, and No. 61/406,998 filed Oct. 26, 2010. Applicant claims the benefits of 35 U.S.C. '120 as to the PCT application and priority under 35 U.S.C. '119 as to the said United States provisional application, and the entire disclosures of both applications are incorporated herein by reference in their entireties.

CROSS-REFERENCE TO RELATED APPLICATIONS

This application claims priority of U.S. provisional patent applications 61/406,997, filed Oct. 26, 2010, and 61/406,998, filed Oct. 26, 2010, the specifications of which are hereby incorporated by reference.

BACKGROUND (a) Field

The subject matter disclosed generally relates to compositions, and more specifically to transdermal or topical compositions comprising nitric oxide amino acid ester compounds improving vascular circulation, and prophylaxis or treatment of a condition associated with impaired blood circulation.

(b) Related Prior Art

The decline in cardiovascular morbidity and mortality in the United States over the past three decades has been the result of significant advances in research on cardiovascular disease mechanisms and therapeutic strategies. However these advances have not been as pronounced in the treatment of peripheral vascular insufficiencies due to the onset of various ailments such as diabetes, and arteriosclerosis. These peripheral insufficiencies result in various disease states and even amputation. The incidence of amputation related to peripheral vascular insufficiency and its related conditions is associated with significant costs and significant impairment to the individual. Worldwide prevalence estimates of amputation is difficult to obtain, mainly because amputation receives very little attention and resources in countries where survival is low (Aleccia 2010). The overall rates of amputation due to trauma or malignancy are decreasing while the incidence of dysvascular amputations is rising (Dillingham et al. 2002). Amputations due to dysvascular disease accounts from roughly 54% of limb loss cases in the United States, while traumatic amputations account for 45% of loss (Aleccia 2010). The number of lower limb amputations is expected to increase in the United States to 58,000 per year by 2030 (Cutson and Bongiorni 1996; Fletcher et al., 2002), with nearly 75% occurring in those aged 65 and older (Clark et al. 1983).

The compounds administered for the treatment of diuresis, peripheral vascular disease (also known as peripheral arterial disease) and diseases resulting from oxidative and/or endothelial dysfunctions often result in toxic, chronic and/or debilitating side effects. Cardiovascular compounds such as ACE inhibitors, beta-adrenergic blockers, antithrombotic, thrombolytics, anticoagulants, antiplatelet agents and vasodilator compounds or anti-hyperlipidemic compounds, show, for example, respiratory toxicity resulting in asthma and/or bronchitis, renal impairment, liver toxicity and other side effects. Hence there is a need in the art for compounds that have improved efficacy, lower toxicity and that can be used at low dosages. The invention is directed to these, as well as other, important ends.

An ulcer is a sore on the skin or a mucous membrane, accompanied by the disintegration of tissue. Ulcers can result in complete loss of the epidermis and often portions of the dermis and even subcutaneous fat. An ulcer that appears on the skin is often visible as an inflamed tissue with an area of reddened skin. A skin ulcer is often visible in the event of exposure to heat or cold, irritation, or a problem with blood circulation such as the cardiovascular diseases mentioned above. For example, due to lack of mobility, there is a prolonged pressure on the tissues, which causes a stress in the blood circulation which is transformed to a skin ulcer, commonly known as bedsores or decubitus ulcers. Ulcers often become infected, and pus forms.

Nitric oxide (NO) donor molecules are well known vasodilators that can contribute to improving blood circulation in an ulcerated area. Molecules such as nitroglycerin have been used to treat such conditions. However, in the case of nitroglycerin, there are several drawbacks to the manufacture, storage and use of nitroglycerin. Nitroglycerin is an explosive compound that is difficult to produce and stabilize. It is inherently unstable over the long term resulting in a maximum shelf life of a product containing of about six months.

A major drawback to the long term usage of nitroglycerin for the treatment of diseases is that the metabolic pathway for the liberation of nitric oxide from nitroglycerin occurs in the mitochondria, utilizing the aldehyde dehydrogenase 2 enzyme. The liberation of large amounts of nitric oxide within the mitochondria from the use of nitroglycerin proves to be toxic to the mitochondria over time and eventually causes extensive metabolic disruption. Also, certain classes of patient suffering from nitric oxide deficiencies, mainly of Asian descent, have been shown to carry a recessive allele of the gene producing aldehyde dehydrogenase 2 which renders them non-responsive to the use of nitroglycerin.

Therefore there still exists a need for an efficient replacement molecules for nitroglycerin, but that would not possess the negative aspects of nitroglycerin, such as poor stability, short half life and inherent toxicity. The use of such replacement molecules for the treatment for dermatological ulcers, is highly desirable.

It is thus desirable to provide a composition and method for improving vascular circulation, and prophylaxis or treatment of a condition associated with impaired blood circulation, which involves an alternative compound to nitroglycerin, and does not require any special operational procedures other than the application of a composition.

It is thus desirable to provide a composition and method for improving vascular circulation, and prophylaxis or treatment of a condition associated with impaired blood circulation which contains an alternative compound to currently existing vasodilator compounds, and does not require any special operational procedures other than the application of a composition.

SUMMARY

According to an embodiment, there is provided a method of a method of improving vascular circulation, and prophylaxis or treatment of a condition associated with impaired blood circulation in a patient which comprises:
(a) treating the patient with a therapeutically effective amount of a compound of formula (I)

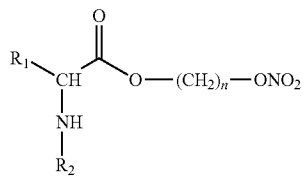
(I)

wherein n may be 1 to 10;
wherein $R_1$ may be an amino acid side chain group (D or L configuration),
wherein $R_2$ may be a hydrogen atom, or an amino acid (D or L configuration) forming a peptide bond, or any pharmaceutically acceptable salts thereof.

The compound of formula (I) may be (2-nitrooxy)-2-ethylamino-3-methylbutanoate:

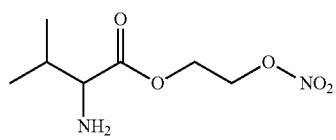

or any pharmaceutically acceptable salts thereof.
The compound of formula (I) may be valine butylene glycol nitrate:

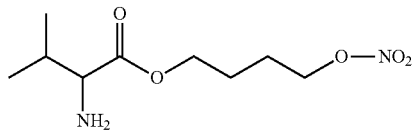 [SMILES: CC(C)C(N)C(=O)OCCCCO[N+](=O)[O-]]

or any pharmaceutically acceptable salts thereof.
The compound of formula (I) may be:

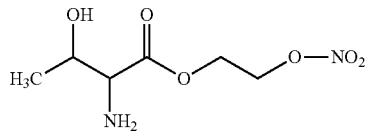

or any pharmaceutically acceptable salts thereof.
The compound of formula (I) may be 2'-nitrooxyethyl 2-amino-pentanoate:

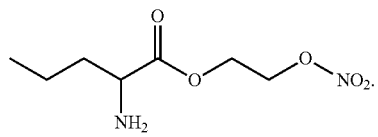

or any pharmaceutically acceptable salts thereof.
The method as claimed in claim 1, wherein said compound of formula (I) is 4'-nitrooxybutyl 2-amino-pentanoate:

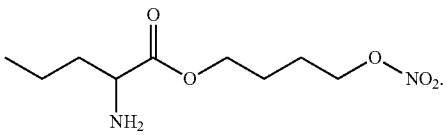 [SMILES: CCCC(N)C(=O)OCCCCO[N+](=O)[O-]]

or any pharmaceutically acceptable salts thereof.
The $R_2$ may be a hydrogen atom.
The $R_1$ may be chosen from:

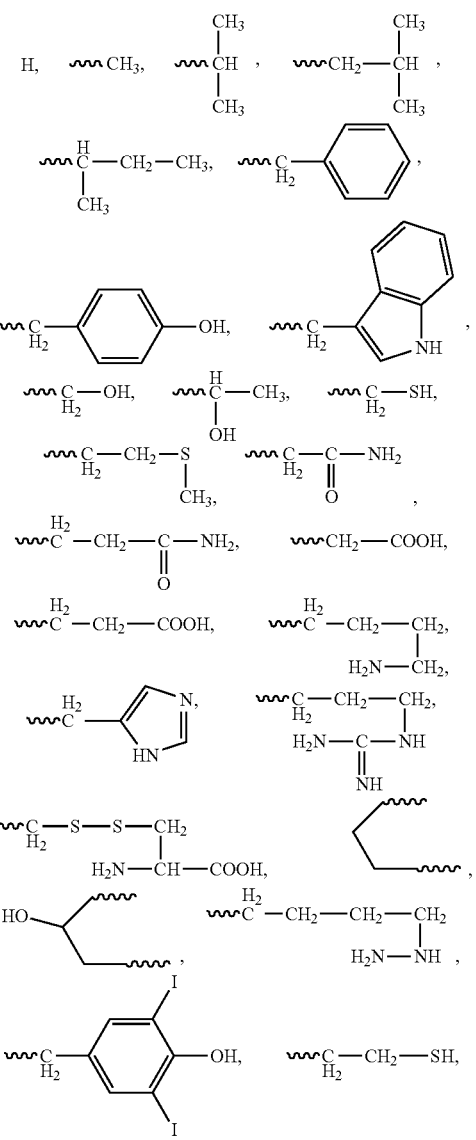

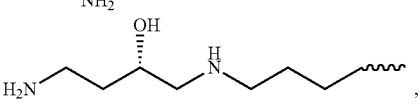

wherein when $R_1$ is

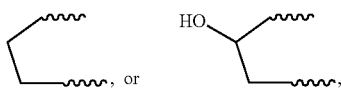

said $R_1$ may be also linked to an $NH_2$ of said Formula (I) to form a proline or hydroxyproline amino acid side chain.

The $R_2$ may be an amino acid of formula (II) (D or L configuration) forming a peptide bond:

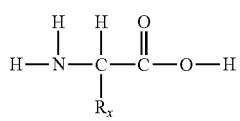
(II)

wherein $R_x$ may be chosen from

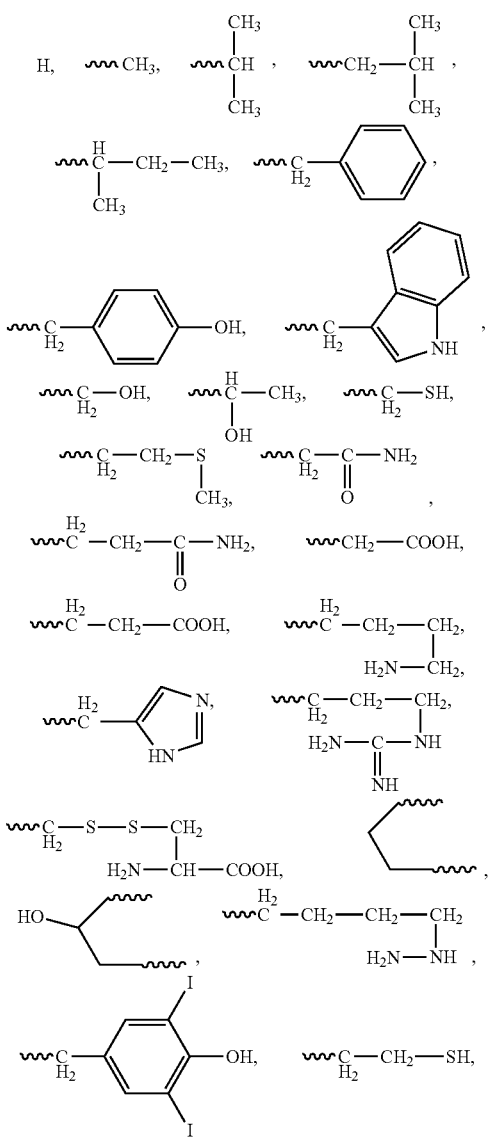

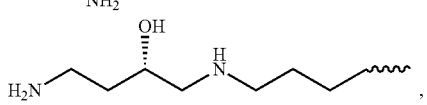

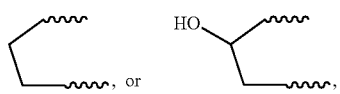

wherein when $R_1$ is

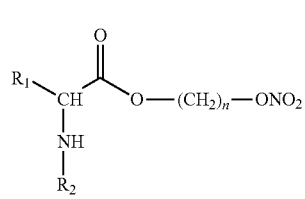

said $R_1$ may be also linked to an $NH_2$ of said Formula (I) to form a proline or hydroxyproline amino acid side chain.

The treating may be transdermally or topically.

The condition associated with impaired blood circulation may be chosen from a skin ulcer, a decubitus ulcer, a mouth ulcer, a diabetic foot ulcer, a venous insufficiency ulcer, a venous ulcer, an arterial insufficiency ulcer, a neuropathic ulcer, a genital ulcer, a sore, a wound, a peripheral vascular disease, an atherosclerosis, Raynaud's phenomenon, an erythromelalgia and a gangrene.

The peripheral vascular disease may be associated with diabetes.

The patient may have a normotensive blood pressure, a hypertensive blood pressure, or a hypotensive blood pressure.

The blood pressure may be a normotensive blood pressure or a hypotensive blood pressure, and treating the patient results in a stable blood pressure.

The blood pressure may be a hypertensive blood pressure, and treating the patient results in a decreased blood pressure.

The decreased blood pressure is a normotensive blood pressure.

According to another embodiment, there is provided a use of a compound of formula (I) for the preparation of a medicament for the treatment and/or alleviation of a peripheral vascular disease:

$$R_1-\underset{\underset{R_2}{NH}}{CH}-\overset{O}{\underset{}{C}}-O-(CH_2)_n-ONO_2$$ (I)

wherein n may be 1 to 10;

wherein $R_1$ may be an amino acid side chain group (D or L configuration), wherein $R_2$ may be a hydrogen atom, or an amino acid (D or L configuration) forming a peptide bond, or any pharmaceutically acceptable salts thereof.

According to another embodiment, there is provided a use of a compound of formula (I) for the treatment and/or alleviation of a peripheral vascular disease:

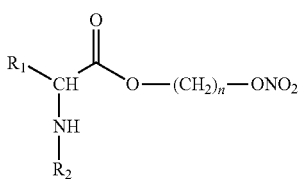
(I)

wherein n may be 1 to 10;

wherein $R_1$ may be an amino acid side chain group (D or L configuration), wherein $R_2$ may be a hydrogen atom, or an amino acid (D or L configuration) forming a peptide bond, or any pharmaceutically acceptable salts thereof.

According to another embodiment, there is provided a use of a compound of formula (I) for the preparation of a medicament for improving vascular circulation, and prophylaxis or treatment of a condition associated with impaired blood circulation:

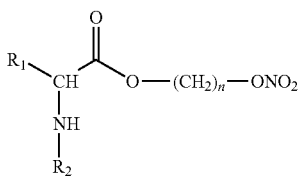
(I)

wherein n may be 1 to 10;

wherein $R_1$ may be an amino acid side chain group (D or L configuration), wherein $R_2$ may be a hydrogen atom, or an amino acid (D or L configuration) forming a peptide bond, or any pharmaceutically acceptable salts thereof.

According to another embodiment, there is provided a use of a compound of formula (I) for improving vascular circulation, and prophylaxis or treatment of a condition associated with impaired blood circulation:

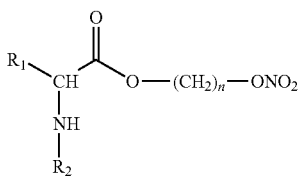
(I)

wherein n may be 1 to 10;

wherein $R_1$ may be an amino acid side chain group (D or L configuration), wherein $R_2$ may be a hydrogen atom, or an amino acid (D or L configuration) forming a peptide bond, or any pharmaceutically acceptable salts thereof.

The compound of formula (I) may be (2-nitrooxy)-2-ethylamino-3-methylbutanoate:

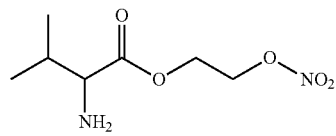

or any pharmaceutically acceptable salts thereof.

The compound of formula (I) may be valine butylene glycol nitrate:

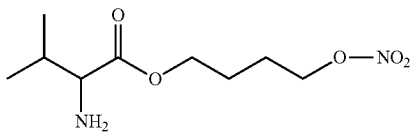 [SMILES: CC(C)C(N)C(=O)OCCCCO[N+](=O)[O-]]

or any pharmaceutically acceptable salts thereof.

The compound of formula (I) may be:

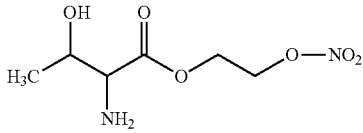

or any pharmaceutically acceptable salts thereof.

The compound of formula (I) may be 2'-nitrooxyethyl 2-amino-pentanoate:

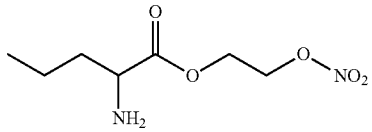

or any pharmaceutically acceptable salts thereof.

The compound of formula (I) may be 4'-nitrooxybutyl 2-amino-pentanoate:

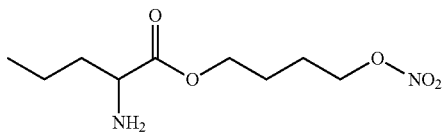 [SMILES: CCCC(N)C(=O)OCCCCO[N+](=O)[O-]]

or any pharmaceutically acceptable salts thereof.

The compound of formula (I) wherein $R_2$ may be a hydrogen atom.

The compound of formula (I), wherein $R_1$ is chosen from:

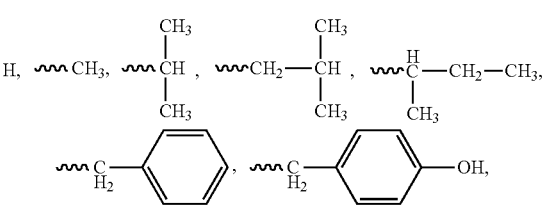

-continued

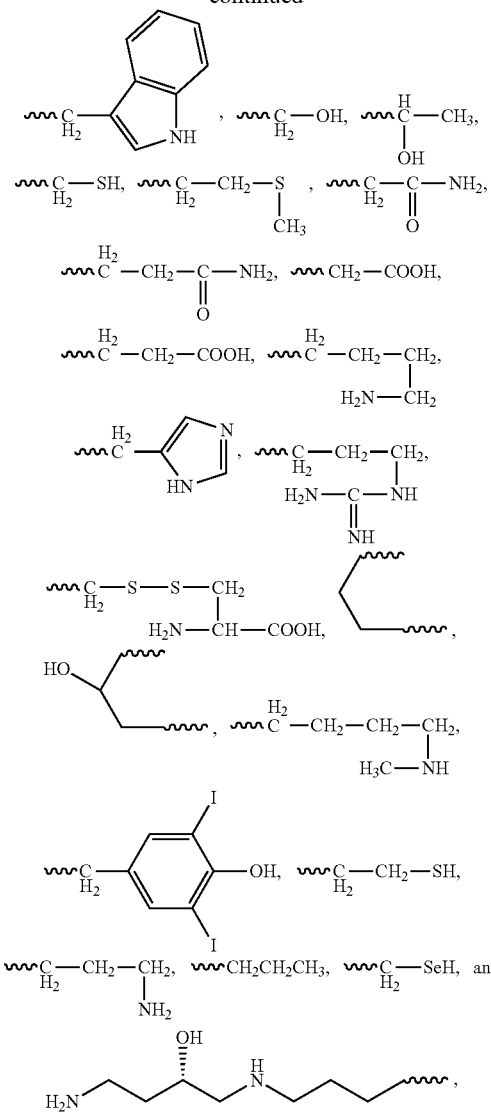

wherein when $R_1$ is

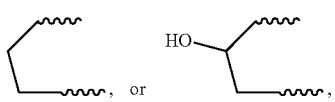

said $R_1$ may be linked to an $NH_2$ of said Formula (I) to form a proline or hydroxyproline amino acid side chain.

The $R_2$ may be an amino acid of formula (II) (D or L configuration) forming a peptide bond:

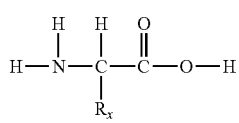

(II)

wherein $R_x$ may be chosen from;

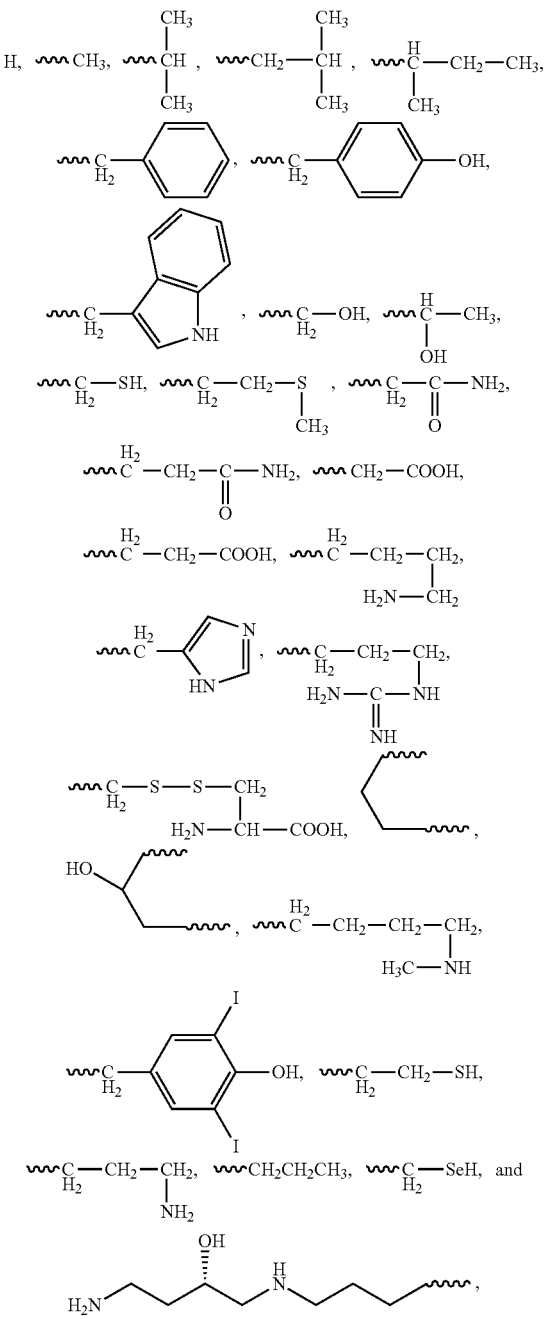

wherein when $R_1$ is

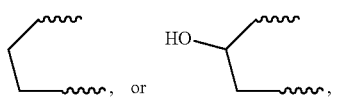

said $R_1$ may be also linked to an $NH_2$ of said Formula (I) to form a proline or hydroxyproline amino acid side chain.

The condition associated with impaired blood circulation may be chosen from a skin ulcer, a decubitus ulcer, a mouth ulcer, a diabetic foot ulcer, a venous insufficiency ulcer, a venous ulcer, an arterial insufficiency ulcer, a neuropathic ulcer, a genital ulcer, a sore, a wound, a peripheral vascular disease, an atherosclerosis, Raynaud's phenomenon, erythromelalgia and a gangrene.

The peripheral vascular disease may be associated with diabetes.

According to another embodiment, there is provided a topical composition for improving vascular circulation and prophylaxis or treatment of peripheral vascular disease and a condition associated with impaired blood circulation comprising:

(a) an effective amount of a compound of formula (I):

$$R_1-\underset{\underset{R_2}{\overset{|}{NH}}}{\overset{|}{CH}}-\overset{O}{\overset{\|}{C}}-O-(CH_2)_n-ONO_2 \quad (I)$$

wherein n may be 1 to 10;
wherein $R_1$ may be an amino acid side chain group (D or L configuration),
wherein $R_2$ may be a hydrogen atom, or an amino acid (D or L configuration) forming a peptide bond, or any pharmaceutically acceptable salts thereof; and
(b) at least one topical antimicrobial,
in association with a pharmaceutically acceptable topical carrier.

The compound of formula (I) may be (2-nitrooxy)-2-ethylamino-3-methylbutanoate:

or any pharmaceutically acceptable salts thereof.
The compound of formula (I) may be valine butylene glycol nitrate:

or any pharmaceutically acceptable salts thereof.
The compound of formula (I) may be:

or any pharmaceutically acceptable salts thereof.
The compound of formula (I) may be 2'-nitrooxyethyl 2-amino-pentanoate:

or any pharmaceutically acceptable salts thereof.
The compound of formula (I) may be 4'-nitrooxybutyl 2-amino-pentanoate:

or any pharmaceutically acceptable salts thereof.
The $R_2$ may be a hydrogen atom.
The $R_1$ may be chosen from:

-continued

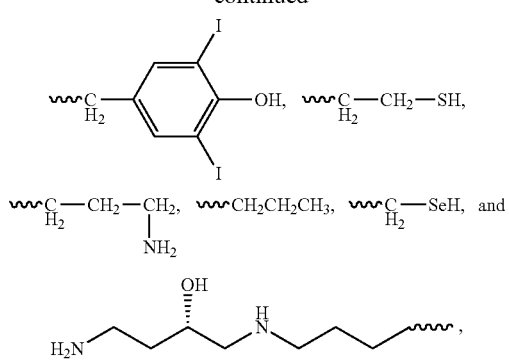

wherein when $R_1$ is

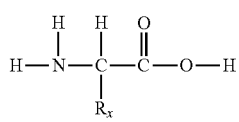

said $R_1$ may be also linked to an $NH_2$ of said Formula (I) to form a proline or hydroxyproline amino acid side chain.

The $R_2$ may be an amino acid of formula (II) (D or L configuration) forming a peptide bond:

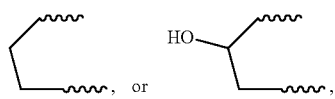

(II)

wherein $R_x$ may be chosen from;

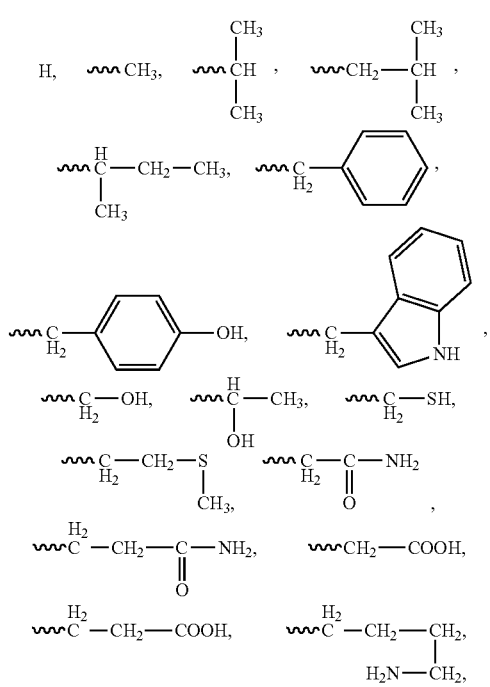

-continued

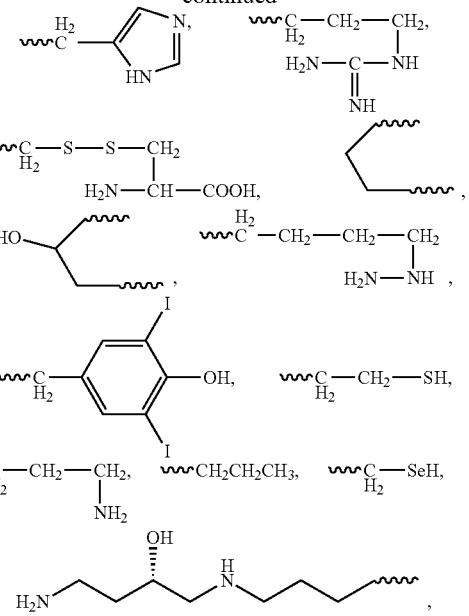

wherein when $R_1$ is

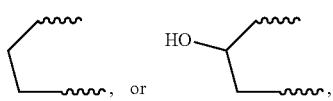

said $R_1$ may be also linked to an $NH_2$ of said Formula (I) to form a proline or hydroxyproline amino acid side chain.

The topical antimicrobial may be at least one of a topical antibiotic, a topical antifungal, and combinations thereof.

The topical antibiotic may be chosen from Amikacin, Gentamicin, Kanamycin, Neomycin, Netilmicin, Tobramycin, Paromomycin, Geldanamycin, Herbimycin, Loracarbef, Ertapenem, Doripenem, Imipenem/Cilastatin, Meropenem, Cefadroxil, Cefazolin, Cefalotin, Cefalexin, Cefaclor, Cefamandole, Cefoxitin, Cefprozil, Cefuroxime, Cefixime, Cefdinir, Cefditoren, Cefoperazone, Cefotaxime, Cefpodoxime, Ceftazidime, Ceftibuten, Ceftizoxime, Ceftriaxone, Cefepime, Ceftobiprole, Teicoplanin, Vancomycin, Telavancin, Clindamycin, Lincomycin, Azithromycin, Clarithromycin, Dirithromycin, Erythromycin, Roxithromycin, Troleandomycin, Telithromycin, Spectinomycin, Aztreonam, Furazolidone, Nitrofurantoin, Amoxicillin, Ampicillin, Azlocillin, Carbenicillin, Cloxacillin, Dicloxacillin, Flucloxacillin, Mezlocillin, Methicillin, Nafcillin, Oxacillin, Penicillin G, Penicillin V, Piperacillin, Temocillin, Ticarcillin, Amoxicillin and clavulanate, Ampicillin and sulbactam, Piperacillin and tazobactam, Ticarcillin and clavulanate, Bacitracin, Colistin, Polymyxin B, Ciprofloxacin, Enoxacin, Gatifloxacin, Levofloxacin, Lomefloxacin, Moxifloxacin, Nalidixic acid, Norfloxacin, Ofloxacin, Trovafloxacin, Grepafloxacin, Sparfloxacin, Temafloxacin, Mafenide, Sulfonamidochrysoidine, Sulfacetamide, Sulfadiazine, Silver sulfadiazine, Sulfamethizole, Sulfamethoxazole, Sulfanilimide, Sulfasalazine, Sulfisoxazole, Trimethoprim, Trimethoprim-Sulfamethoxazole, Demeclocycline, Doxycycline, Minocycline, Oxytetracycline, Tetracycline, Clofazimine, Dapsone, Capreomycin, Cycloserine, Ethambutol, Ethionamide, Isoniazid, Pyrazinamide, Rifampicin, Rifabutin, Rifapentine, Streptomycin, Arsphenamine, Chloramphenicol, Fosfomycin, Fusidic acid, Linezolid, Metronidazole, Mupirocin, Platensimycin, Quinupristin/Dalfopristin, Rifaximin, Thiamphenicol, and Tinidazole.

The topical antifungal may be chosen from Natamycin, Rimocidin, Filipin, Nystatin, Amphotericin B, Candicin, Hamycin, Miconazole, Ketoconazole, Clotrimazole, Econazole, Bifonazole, Butoconazole, Fenticonazole, Isoconazole, Oxiconazole, Sertaconazole, Sulconazole, Tioconazole, Fluconazole, Itraconazole, Isavuconazole, Ravuconazole, Posaconazole, Voriconazole, Terconazole, Abafungin, Terbinafine, Amorolfine, Naftifine, Butenafine, Anidulafungin, Caspofungin, Micafungin, Benzoic acid, Ciclopirox, Tolnaftate, Undecylenic acid, 5-fluorocytosine, Griseofulvin, Haloprogin, and Sodium bicarbonate.

The skin penetration enhancer may be chosen from a $C_8$-$C_{22}$ fatty acid, a $C_8$-$C_{22}$ fatty alcohol, a lower alkyl ester of a $C_8$-$C_{22}$ fatty acid, a di(lower)alkyl ester of $C_8$-$C_{22}$ diacid, a monoglyceride of $C_8$-$C_{22}$ fatty acid, tetrahydrofurfuryl alcohol polyethylene glycol ether, polyethylene glycol, propylene glycol, 2-(2-ethoxyethoxy)ethanol (transcutol), diethylene glycol monomethyl ether, diethylene glycol monoethyl ether, an alkylaryl ether of polyethylene oxide, a polyethylene oxide monomethyl ether, a polyethylene oxide dimethyl ether; dimethyl sulfoxide (DMSO), glycerol, ethyl acetate, acetoacetic ester, N-alkylpyrrolidone, a terpenes, dimethyl formamide (DMF), N,N-dimethylacetamide (DMA), methyl laurate, glycerol monolaurate, a fatty acid ester of a $C_2$ to $C_4$ alkanediol having a fatty acid portion of said ester from about 8 to 22 carbon atoms, a fatty alcohol ether of a $C_2$ to $C_4$ alkanediols having a fatty acid portion of said ether from about 8 to 22 carbon atoms, triglycerides of coconut oil, isopropyl palmitate, isopropyl myristate, laurocapram, and combinations thereof.

The $C_8$-$C_{22}$ fatty acid may be chosen from isostearic acid, octanoic acid, and oleic acid.

The $C_8$-$C_{22}$ fatty alcohol may be chosen from oleyl alcohol and lauryl alcohol.

The lower alkyl ester of a $C_8$-$C_{22}$ fatty acid may be chosen from ethyl oleate, isopropyl myristate (IPM), butyl stearate, and methyl laurate.

The di(lower)alkyl esters of a $C_8$-$C_{22}$ diacid may be diisopropyl adipate.

The monoglyceride of a $C_8$-$C_{22}$ fatty acid may be glyceryl monolaurate.

The pharmaceutically acceptable carrier is chosen from a water base or an oil base carrier.

The composition may be further comprising a thickening agent.

The thickening agent may be chosen from CARBOPOL®, carboxypolymethylene, carboxymethylcellulose Carbopol® Ultrez 10, Carbopol® 940, Carbopol® 941, Carbopol® 954, Carbopol® 980, Carbopol® 981, Carbopol® ETD 2001, Carbopol® EZ-2 and Carbopol® EZ-3.

The composition may be further comprising a wetting agent.

The wetting agent may be chosen from benzalkonium chloride, benzethonium chloride, cetylpyridinium chloride; dioctyl sodium sulfosuccinate; a polyoxyethylene alkylphenyl ether, a poloxamers, a polyoxyethylene fatty acid glyceride, a polyoxyethylene alkyl ethers, a polyoxyethylene fatty acid ester, a polyoxyethylene sorbitan ester, a propylene glycol fatty acid ester, sodium lauryl sulfate, sodium laureth sulfate oleic acid, sodium oleate, triethanolamine oleate, a glyceryl fatty acid ester, a sorbitan ester, sorbitan monooleate, sorbitan monopalmitate, sorbitan monostearate, tyloxapol and mixtures thereof.

The composition may be further comprising a lubricant.

The composition lubricant may be chosen from glyceryl behapate, stearic acid, magnesium stearate, calcium stearate, sodium stearate; a hydrogenated vegetable oil, colloidal silica, talc, a waxe, boric acid; sodium benzoate; sodium acetate; sodium fumarate; sodium chloride; DL-leucine; sodium oleate; sodium lauryl sulfate; magnesium lauryl sulfate, glycerol, sorbitol, a water soluble cellulose, a polysorbate, a carbomer, a polyethylene glycol (PEG), a polyethylene, and a thickening agent.

The water soluble cellulose may be chosen from modified starch, methylcellulose, hydroxypropyl cellulose, hydroxypropyl methylcellulose, Methocel® MC, carboxymethyl cellulose, ethyl cellulose, hydroxyl ethyl cellulose, and any combination thereof.

The polysorbate may be chosen from polyoxyethylene (20) sorbitan monolaurate (polysorbate 20), polyoxyethylene (20) sorbitan monopalmitate (polysorbate 40), polyoxyethylene (20) sorbitan monostearate (polysorban 60), polyoxyethylene (20) sorbitan tristrearate (polysorban 65), and polyoxyethylene (20) sorbitan monooleate (polysorban 80), and any combination thereof.

The carbomer may be a Carbopol® polymer chosen from Carbopol® polymer 71G NF, Carbopol® polymer 971P NF, Carbopol® polymer 974P NF, Carbopol® polymer 980 NF, Carbopol® polymer 981 NF, Carbopol® polymer 5984 EP and Carbopol® polymer Ultrez 10 NF, and any combination thereof.

The polyethylene glycol (PEG) may be chosen from PEG 200, PEG 200E, PEG 300, PEG 300E, PEG 400, PEG 400E, PEG 600 and PEG 600E, and any combination thereof.

The thickening agent may be chosen from alginic acid, sodium alginate, potassium alginate, ammonium alginate, calcium alginate, agar, carrageenan, locust bean gum, xanthan gum, pectin, and gelatin, and any combination thereof.

The composition may be further comprising at least one antiseptic agent.

The antiseptic agent may be selected from chlorhexidine gluconate, glucono delta-lactone, a paraben compound, benzoic acid, imidazolidinyl urea, a quaternary ammonium compound, methyl hydroxybenzoate, propyl hydroxybenzoate, chlorocresol, benzalkonium chloride and Octenidine dihydrochloride.

The composition may be further comprising a preservative agent.

The preservative agent may be chosen from EDTA, EGTA, hydroxytoluene butoxide, hydroxyanisol butoxide, sodium hydroxide, calcium propionate, sodium nitrate, sodium nitrite, sulfur dioxide, sodium bisulfite, and potassium hydrogen sulfite.

The composition may be further comprising an emollient.

The emollient may be chosen from mineral oil, a mixture of a mineral oil and a lanolin alcohol, cetyl alcohol, cetostearyl alcohol, petrolatum, petrolatum and a lanolin alcohol, cetyl esters wax, cholesterol, glycerin, glyceryl monostearate, isopropyl myristate (IPM), isopropyl palmitate, lecithin, allyl caproate, althea officinalis extract, arachidyl alcohol, argobase EUC, butylene glycol, dicaprylate/dicaprate, acacia, allantoin, carrageenan, cetyl dimethicone, cyclomethicone, diethyl succinate, dihydroabietyl behenate, dioctyl adipate, ethyl laurate, ethyl palmitate, ethyl stearate, isoamyl laurate, octanoate, PEG-75, lanolin, sorbitan laurate, walnut oil, wheat germ oil, super refined almond, super refined sesame, super refined soybean, octyl palmitate, caprylic/capric triglyceride, butyrospermum parkii oil, olive oil, cetyl alcohol, behenyl alcohol, limnanthes alba seed oil, palmitic acid and glyceryl cocoate.

The composition may be further comprising a fragrance.

The composition may be one of a gel and a transdermal composition.

According to another embodiment, there is provided a method of treating an ulcer in a patient which comprises:
(a) treating said patient with the composition according to the present invention, to treat said ulcer.

The following terms are defined below.

The term "Amino acid ester compound" is intended to mean the condensation product of an amino acid with mononitrated alkane ou alkene diol. As will be evident to those familiar to the art, the condensation reaction could also involve, but not limited to, dipeptides or tripeptides, nitrated alcohols containing aliphatic, alkyl or aromatic moieties, as well as other nitric oxide groups attached to the alkane or alkene diols. Amino acid or dipeptide reactions are preferred as well as the condensation reaction with short chain mononitrated alkane diols such as 1,3 propanediol or 1,4 butanediol.

The expression "Therapeutically effective amount" is intended to mean the amount of the compound and/or composition that is effective to achieve its intended purpose.

The expression "Transdermally absorbed" is intended to mean the delivery of a compound by passage through the skin and into the blood stream.

The terms "Carriers" or "vehicles" are intended to mean carrier materials suitable for compound administration and include any such material known in the art such as, for example, any liquid, lotion, gel, solvent, liquid diluent, solubilizer, or the like.

The term "Nitric oxide adduct" or "NO adduct" is intended to mean compounds and functional groups which, under physiological conditions, can donate, release and/or directly or indirectly transfer any of the three redox forms of nitrogen monoxide ($NO^+$, $NO^-$, $NO^*$), such that the biological activity of the nitrogen monoxide species is expressed at the intended site of action.

The term "Nitric oxide releasing" or "nitric oxide donating" is intended to mean methods of donating, releasing and/or directly or indirectly transferring any of the three redox forms of nitrogen monoxide ($NO+$, $NO-$, $NO^*$), such that the biological activity of the nitrogen monoxide species is expressed at the intended site of action.

The term "Nitric oxide donor" or "NO donor" is intended to mean compounds that donate, release and/or directly or indirectly transfer a nitrogen monoxide species, and/or stimulate the endogenous production of nitric oxide or endothelium-derived relaxing factor (EDRF) in vivo and/or elevate endogenous levels of nitric oxide or EDRF in vivo and/or are oxidized to produce nitric oxide and/or are substrates for nitric oxide synthase and/or cytochrome P450. "NO donor" also includes compounds that are precursors of L-arginine, inhibitors of the enzyme arginase and nitric oxide mediators.

The term "pharmaceutical acceptable carrier" is intended to mean a preservative solution, a saline solution, an isotonic (about 0.9%) saline solution, or about a 5% albumin solution, suspension, sterile water, phosphate buffered saline, and the like. It is also intended to mean any aqueous or non-aqueous solvents that are suitable for delivery of medicine to or into the target organ, as described herein. Other buffering agents, dispersing agents, and inert non-toxic substances suitable for delivery to a patient may be included in the compositions of the present invention. The compositions may be solutions, suspensions or any appropriate formulation suitable for administration, and are typically sterile and free of undesirable particulate matter. The compositions may be sterilized by conventional sterilization techniques.

The term "lubricant" is intended to mean a substance (often a liquid) introduced between two moving surfaces to reduce the friction between them, hydrate the surface as well as reducing wear of the body parts.

The expression "improving vascular circulation" is intended to mean a therapeutic intervention that improves an impaired blood circulation in arteries, veins or both.

The expression "condition associated with impaired blood circulation" is any condition that may result from poor arterial and/or venous blood flow, and may include for example ulcers caused by cold, heat, inflammation or irritation that may cause stress in the blood flow, wounds, sores, discoloration of the affected tissues, gangrene, necrosis, and the likes.

Features and advantages of the subject matter hereof will become more apparent in light of the following detailed description of selected embodiments, as illustrated in the accompanying figures. As will be realized, the subject matter disclosed and claimed is capable of modifications in various respects, all without departing from the scope of the claims. Accordingly, the drawings and the description are to be regarded as illustrative in nature, and not as restrictive and the full scope of the subject matter is set forth in the claims.

Further features and advantages of the present disclosure will become apparent from the following detailed description.

DETAILED DESCRIPTION OF THE PREFERRED EMBODIMENTS

The composition of the present invention contains vasoactive amino acid ester compounds. The nitric oxide amino acid ester compounds of the present invention possess many of the required characteristics necessary to fulfill the role of a primary boosting of NO levels. The compounds easily dissociate in water into the amino acid derivative and associated ion forming the pharmaceutical salt. The compounds of the present invention are extremely stable in the form of the salts, and thus possess long shelf lives and stability.

The nitric oxide releasing groups of the compounds of the present invention are preferably nitro groups (i.e. $NO_2$), nitroso groups (i.e. NO) and/or heterocyclic nitric oxide donor groups that are linked to the amino acid ester compounds through one or more sites such as oxygen (hydroxyl condensation), sulfur (sulfhydryl condensation) and/or nitrogen. The heterocyclic nitric oxide donor groups are preferably furoxans, sydnonimines, oxatriazole-5-ones and/or oxatriazole-5-imines.

The preferred compounds of the present invention are the valine or norvaline derivatives of the nitric oxide amino acid ester of the present invention. The most preferred compounds are known as valine nitrooxy ethyl ester (or valine ethylene glycol nitrate), valine nitrooxy butyl ester (or valine butylene glycol nitrate), or any pharmaceutically acceptable salt thereof, which possess many of the required characteristics necessary to fulfill the role of boosting NO levels. The compound easily dissociates in water into the valine derivative valine ethylene or butylene glycol nitrate and the salt forming acid. The compounds are extremely stable in the form of the salt and thus possesses a long shelf life. It has been observed that the preferred compounds of the present invention do not cause hypotension in normotensive or hypotensive individuals. Therefore, upon administration of the preferred compounds of the present invention, an hypertensive individual will experience the vasodilatory effect caused by the preferred compounds, which will result in a decrease in blood pressure. The decrease in blood pressure may be up to a normotensive blood pressure. Individuals with normal blood pressure will not experience the vasodilatory effect caused by the preferred compounds, and their blood pressure will remain stable (unchanged). Individuals with lower than normal blood pressure (hypotensive) will not experience a further drop in blood pressure and their blood pressure will remain stable (unchanged). Furthermore, the preferred compounds of the present invention have half-life of approximately 5 hours. Preferably, a therapeutically effective amount of the compounds of the present invention are administered. Therapeutically effective amounts include but are not limited to 0.5 to 30 mg of the compound of the present invention. Preferably, therapeutically effective amounts include 1 to 15 mg, 0.5 to 5 mg, 1 to 5 mg, 5 to 10 mg, 10 to 15 mg, 1 to 15 mg, 1 to 30 mg, 5 to 20 mg, 5 to 15 mg, 5 to 30 mg, 10 to 20 mg, 10 to 30 mg and 15 to 30 mg. Other preferable therapeutically effective amounts also include from about 0.05 mg to about 200 mg, or from about 0.05 mg to about 150 mg, or from about 0.05 mg to about 100 mg, or from about 0.05 mg to about 50 mg, or from about 0.05 mg to about 40 mg, or from about 0.05 to about 30 mg, or from about 0.05 mg to about 20 mg, or from about 0.05 mg to about 15 mg, or from about 0.05 mg to about 10 mg, or from about 0.05 mg to about 5 mg, or from about 0.05 mg to about 1 mg, or from about 0.05 mg to about 0.5 mg, about 0.5 mg to about 200 mg, or from about 0.5 mg to about 150 mg, or from about 0.5 mg to about 100 mg, or from about 0.5 mg to about 50 mg, or from about 0.5 mg to about 40 mg, or from about 0.5 to about 30 mg, or from about 0.5 mg to about 20 mg, or from about 0.5 mg to about 15 mg, or from about 0.5 mg to about 10 mg, or from about 0.5 mg to about 5 mg, or from about 0.5 mg to about 1 mg, about 1 mg to about 200 mg, or from about 1 mg to about 150 mg, or from about 1 mg to about 100 mg, or from about 1 mg to about 50 mg, or from about 1 mg to about 40 mg, or from about 1 to about 30 mg, or from about 1 mg to about 20 mg, or from about 1 mg to about 15 mg, or from about 1 mg to about 10 mg, or from about 1 mg to about 5 mg, about 5 mg to about 200 mg, or from about 5 mg to about 150 mg, or from about 5 mg to about 100 mg, or from about 5 mg to about 50 mg, or from about 5 mg to about 40 mg, or from about 5 to about 30 mg, or from about 5 mg to about 20 mg, or from about 5 mg to about 15 mg, or from about 5 mg to about 10 mg, about 10 mg to about 200 mg, or from about 10 mg to about 150 mg, or from about 10 mg to about 100 mg, or from about 10 mg to about 50 mg, or from about 10 mg to about 40 mg, or from about 10 to about 30 mg, or from about 10 mg to about 20 mg, or from about 10 mg to about 15 mg, about 15 mg to about 200 mg, or from about 15 mg to about 150 mg, or from about 15 mg to about 100 mg, or from about 15 mg to about 50 mg, or from about 15 mg to about 40 mg, or from about 15 to about 30 mg, or from about 15 mg to about 20 mg, 20 mg to about 200 mg, or from about 20 mg to about 150 mg, or from about 20 mg to about 100 mg, or from about 20 mg to about 50 mg, or from about 20 mg to about 40 mg, or from about 20 to about 30 mg, about 30 mg to about 200 mg, or from about 30 mg to about 150 mg, or from about 30 mg to about 100 mg, or from about 30 mg to about 50 mg, or from about 30 mg to about 40 mg, about 40 mg to about 200 mg, or from about 40 mg to about 150 mg, or from about 40 mg to about 100 mg, or from about 40 mg to about 50 mg, 50 mg to about 200 mg, or from about 50 mg to about 150 mg, or from about 50 mg to about 100 mg, about 100 mg to about 200 mg, or from about 100 mg to about 150 mg, or 150 mg to about 200 mg.

The compounds and compositions of the invention are described in more detail herein.

The compounds and compositions of the invention can be formulated as pharmaceutically acceptable salt forms. Pharmaceutically acceptable salts include, for example, alkali metal salts and addition salts of free acids or free bases. The nature of the salt is not critical, provided that it is pharmaceutically acceptable. Suitable pharmaceutically-acceptable acid addition salts may be prepared from an inorganic acid or from an organic acid. Examples of such inorganic acids include, but are not limited to, hydrochloric, hydrobromic, hydroiodic, nitric, carbonic, sulfuric and phosphoric acid and the like. Appropriate organic acids include, but are not limited to, aliphatic, cycloaliphatic, aromatic, heterocyclic, carboxylic and sulfonic classes of organic acids, such as, for example, formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, stearic, algenic, β-hydroxybutyric, cyclohexylaminosulfonic, galactaric and galacturonic acid and the like. Suitable pharmaceutically acceptable base addition salts include, but are not limited to, metallic salts made from aluminum, calcium, lithium, magnesium, potassium, sodium and zinc or organic salts made from primary, secondary and tertiary amines, cyclic amines, N,N'-dibenzylethylenediamine, chloroprocaine, choline, diethanolamine, ethylenediamine, meglumine (N-methylglucamine) and procaine and the like. All of these salts may be prepared by conventional means from the corresponding compound by reacting, for example, the appropriate acid or base with the compound. In one embodiment, the pharmaceutically acceptable salts of the compounds of the invention include the nitrate salts. In another embodiment, the pharmaceutically acceptable salts of the compounds of the invention are heterocyclic compounds such as, furoxan, a sydnonimine, an oxatriazole-5-one and/or an oxatriazole-5-imine.

The compounds of the present invention, because of the small size of the molecule, can be other choices of linkages and/or amino acids or their derivatives. For example, as alternatives to the above choices, propyl, butyl, or longer chains may be linked to any amino acid. Salts such as chloride or hydrochloride salts may be used. Other amino acid derivatives may also be chosen. Derivatives of the base amino acids whether they are in the L or D configuration of these amino acids can be chosen. Non standard amino acids, or synthetic derivative of standard and non-standard amino acids may be elected, such as those containing acetyl groups attached to the amide of the molecule or nor derivatives of the amino acids, when such derivatives can be achieved.

The amino acid esters compounds may be based on natural, non-standard or even modified amino acids, with the basic structure as depicted below, where the $R_x$ represents the side chain of the amino acid (wherein $R_x$ may be $R_1$, or $R_2$, as applicable to the specific molecule described herein):

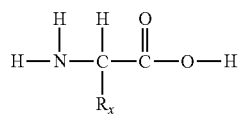

Basic Amino Acid Structure

Natural Amino Acids

| N° | Originating Amino acid | Formula | $R_x = R_1$ or $R_2$ |
|---|---|---|---|
| 1 | Glycine | H | —H |
| 2 | Alanine | $CH_3$ | ∼∼ $CH_3$ |
| 3 | Valine* | $CH(CH_3)_2$ | ∼∼CH($CH_3$)($CH_3$) |
| 4 | Leucine* | $CH_2CH(CH_3)_2$ | ∼∼$CH_2$—CH($CH_3$)($CH_3$) |
| 5 | Isoleucine* | $CH(CH_3)CH_2CH_3$ | ∼∼CH($CH_3$)—$CH_2$—$CH_3$ |
| 6 | Phenylalanine* | $CH_2C_6H_5$ | ∼∼$CH_2$—$C_6H_5$ |
| 7 | Tyrosine | $CH_2C_6H_4OH$ | ∼∼$CH_2$—$C_6H_4$—OH |
| 8 | Tryptophane* | $C_9H_8N$ | ∼∼$CH_2$—(indol-3-yl) |
| 9 | Serine | $CH_2OH$ | ∼∼$CH_2$—OH |
| 10 | Threonine* | $CH(OH)CH_3$ | ∼∼CH(OH)—$CH_3$ |
| 11 | Cysteine | $CH_2SH$ | ∼∼$CH_2$—SH |
| 12 | Methionine* | $CH_2CH_2SCH_3$ | ∼∼$CH_2$—$CH_2$—S—$CH_3$ |
| 13 | Proline | $C_5H_9NO_2$ | pyrrolidine-2-COOH |
| 14 | Asparagine | $CH_2COCH_2$ | ∼∼$CH_2$—C(=O)—$NH_2$ |
| 15 | Glutamine | $CH_2CH_2CONH_2$ | ∼∼$CH_2$—$CH_2$—C(=O)—$NH_2$ |
| 16 | Aspartic acid | $CH_2COOH$ | ∼∼$CH_2$—COOH |
| 17 | Glutamic acid | $CH_2CH_2COOH$ | ∼∼$CH_2$—$CH_2$—COOH |
| 18 | Lysine* | $CH_2CH_2CH_2CH_2NH_2$ | ∼∼$CH_2$—$CH_2$—$CH_2$—$CH_2$—$NH_2$ |
| 19 | Histidine* | $CH_3C_3N_2H_3$ | ∼∼$CH_2$—(imidazol-4-yl) |
| 20 | Arginine* | $(CH_2)_3CN_3H_4$ | ∼∼$CH_2$—$CH_2$—$CH_2$—NH—C(=NH)—$NH_2$ |

*essential amino acids

Modified Amino Acids

| N° | Originating Amino acid | Formula | $R_x = R_1$ or $R_2$ |
|---|---|---|---|
| A | Cystine | $CH_2S_2CH_2CHNH_2COOH$ | ∼∼$CH_2$—S—S—$CH_2$—CH($NH_2$)—COOH |
| B | Hydroxyproline | $C_5H_9NO_3$ | 4-hydroxy-pyrrolidine-2-COOH |
| C | ε-N-methyllysine | $CH_2CH_2CH_2CH_2NHCH_3$ | ∼∼$CH_2$—$CH_2$—$CH_2$—$CH_2$—NH—$CH_3$ |

| N° | Originating Amino acid | Formula | $R_x = R_1$ or $R_2$ |
|---|---|---|---|
| D | diiodotyrosine | $CH_2C_6H_2I_2OH$ | 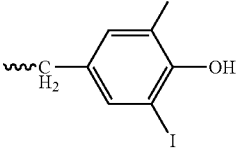 |
| E | homocysteine | $CH_2CH_2SH$ | 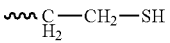 |
| F | ornithine | $CH_2CH_2CH_2NH_2$ | 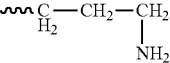 |
| G | Norvaline | $CH_2—CH_2—CH_3$ | $CH_2CH_2CH_3$ |
| H | selenocysteine | $CH_2—SeH$ | 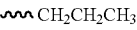 |
| I | Hypusine | $CH_2CH_2CH_2CH_2NHCH_2CH(OH)CH_2CH_2NH_2$ | 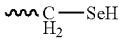 |
| J | Dehydroalanine | $CH_2$ | 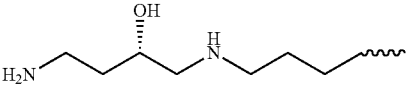 |

The nitric oxide amino acid ester compounds of the present invention are not limited to a single amino acid molecule. The compounds of the present invention may be dipeptide or even tripeptide molecules, with the general formula depicted below and where $R_x$ and $R_y$ independently are any of the amino acid side chains described herein.

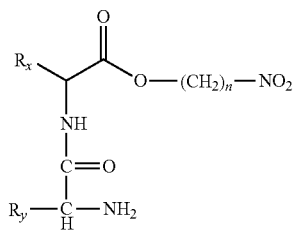

The composition containing a compound as defined in the present invention may include a wide variety of additional components, including, for example, one or more of gases, gaseous precursors, liquids, oils, stabilizing materials, pharmaceutical acceptable carriers, photoactive agents.

Compositions described herein also include those which are suitable for transdermal administration of the compound as define in the present invention and optionally include a vehicle or carrier for the transdermal administration of the compounds described herein as well as further comprising one or more of the following: pharmacologically active agents, solvents, thickening agents, skin penetration enhancers, wetting agents, lubricants, emollients, substances added to mask or counteract a disagreeable odor, fragrances, preservative agents and antiseptic agents.

According to another embodiment, the compositions described herein also include those which are suitable for topical administration, such as in the form of gels and creams, for administration of the compound as defined in the present invention and optionally include a vehicle or carrier for the topical administration of the compounds described herein as well as further comprising one or more of the following: pharmacologically active agents, solvents, thickening agents, skin penetration enhancers, wetting agents, lubricants, emollients, substances added to mask or counteract a disagreeable odor, fragrances, preservative agents and antiseptic agents.

The compounds and compositions of the present invention can be administered transdermally in dosage unit formulations containing conventional nontoxic pharmaceutically acceptable carriers, adjuvants, and vehicles, as desired. In one embodiment of the invention the amino acid ester compound comprising at least one nitric oxide releasing group is administered transdermally or topically.

Transdermal compound administration, which is known to one skilled in the art, involves the delivery of pharmaceutical compounds via percutaneous passage of the compound into the systemic circulation of the patient. Topical administration can also involve the use of transdermal administration such as transdermal patches or iontophoresis devices. Other components can be incorporated into the transdermal patches as well. For example, compositions and/or transdermal patches can be formulated with one or more preservatives or bacteriostatic agents including, but not limited to, methyl hydroxybenzoate, propyl hydroxybenzoate, chlorocresol, benzalkonium chloride, and the like. Dosage forms for topical administration of the compounds and compositions can include creams, sprays, lotions, gels, ointments, eye drops, nose drops, ear drops, and the like. In such dosage forms, the compositions of the invention can be mixed to form white, smooth, homogeneous, opaque cream or lotion with, for example, benzyl alcohol 1% or 2% (wt/wt) as a preservative, emulsifying wax, glycerin, isopropyl palmitat, lactic acid, purified water and sorbitol solution. In addition, the compositions can contain polyethylene glycol 400. They can be mixed to form ointments with, for example, benzyl alcohol 2% (wt/wt) as preservative, white petrolatum, emulsifying wax, and tenox II (butylated hydroxyanisole, propyl gallate, citric acid, propylene glycol). Woven pads or rolls of bandaging material, e.g., gauze, can be impregnated with the compositions in solution, lotion, cream, ointment or other such form can also be used for topical application.

The compositions can also be applied topically using a transdermal system, such as one of an acrylic-based polymer adhesive with a resinous crosslinking agent impregnated with the composition and laminated to an impermeable backing. In a particular embodiment, the compositions of the invention are administered as a transdermal patch, more particularly as a sustained-release transdermal patch. The transdermal patches of the invention can include any conventional form such as, for example, adhesive matrix, polymeric matrix, reservoir patch, matrix or monolithic-type laminated structure, and are generally comprised of one or more backing layers, adhesives, skin penetration enhancers, an optional rate controlling membrane and a release liner which is removed to expose the adhesives prior to application. Polymeric matrix patches also comprise a polymeric-matrix forming material. Suitable transdermal patches are described in more detail in, for example, U.S. Pat. Nos. 5,262,165; 5,948,433; 6,010,715 and 6,071,531.

Topical Antimicrobials

As used herein, "topical antimicrobials" refer to compounds that kill or inhibits the growth of microorganisms such as bacteria, fungi, or protozoans. Antimicrobial drugs either kill microbes (microbicidal) or prevent the growth of microbes (microbistatic). Disinfectants are antimicrobial substances used on non-living objects. Antimicrobials include compounds of diverse categories, such as antibiotics, antivirals, antifungals, antiparasitics. Preferably, the composition according to the present invention will include at least one of an antibiotic and an antifungal.

Skin ulcers may take a very long time to heal and treatment typically tries to avoid the ulcer getting infected. Topical antimicrobials, especially antibiotics, are normally used to prevent the ulcer getting infected and the wound or ulcer is usually kept clear of dead tissue through surgical debridement.

Antibiotics include in a non-limiting manner Amikacin, Gentamicin, Kanamycin, Neomycin, Netilmicin, Tobramycin, Paromomycin, Geldanamycin, Herbimycin, Loracarbef, Ertapenem, Doripenem, Imipenem/Cilastatin, Meropenem, Cefadroxil, Cefazolin, Cefalotin, Cefalexin, Cefaclor, Cefamandole, Cefoxitin, Cefprozil, Cefuroxime, Cefixime, Cefdinir, Cefditoren, Cefoperazone, Cefotaxime, Cefpodoxime, Ceftazidime, Ceftibuten, Ceftizoxime, Ceftriaxone, Cefepime, Ceftobiprole, Teicoplanin, Vancomycin, Telavancin, Clindamycin, Lincomycin, Azithromycin, Clarithromycin, Dirithromycin, Erythromycin, Roxithromycin, Troleandomycin, Telithromycin, Spectinomycin, Aztreonam, Furazolidone, Nitrofurantoin, Amoxicillin, Ampicillin, Azlocillin, Carbenicillin, Cloxacillin, Dicloxacillin, Flucloxacillin, Mezlocillin, Methicillin, Nafcillin, Oxacillin, Penicillin G, Penicillin V, Piperacillin, Temocillin, Ticarcillin, Amoxicillin and clavulanate, Ampicillin and sulbactam, Piperacillin and tazobactam, Ticarcillin and clavulanate, Bacitracin, Colistin, Polymyxin B, Ciprofloxacin, Enoxacin, Gatifloxacin, Levofloxacin, Lomefloxacin, Moxifloxacin, Nalidixic acid, Norfloxacin, Ofloxacin, Trovafloxacin, Grepafloxacin, Sparfloxacin, Temafloxacin, Mafenide, Sulfonamidochrysoidine, Sulfacetamide, Sulfadiazine, Silver sulfadiazine, Sulfamethizole, Sulfamethoxazole, Sulfanilimide, Sulfasalazine, Sulfisoxazole, Trimethoprim, Trimethoprim-Sulfamethoxazole, Demeclocycline, Doxycycline, Minocycline, Oxytetracycline, Tetracycline, Clofazimine, Dapsone, Capreomycin, Cycloserine, Ethambutol, Ethionamide, Isoniazid, Pyrazinamide, Rifampicin, Rifabutin, Rifapentine, Streptomycin, Arsphenamine, Chloramphenicol, Fosfomycin, Fusidic acid, Linezolid, Metronidazole, Mupirocin, Platensimycin, Quinupristin/Dalfopristin, Rifaximin, Thiamphenicol, and Tinidazole.

Antifungal include in a non-limiting manner Natamycin, Rimocidin, Filipin, Nystatin, Amphotericin B, Candicin, Hamycin, Miconazole, Ketoconazole, Clotrimazole, Econazole, Bifonazole, Butoconazole, Fenticonazole, Isoconazole, Oxiconazole, Sertaconazole, Sulconazole, Tioconazole, Fluconazole, Itraconazole, Isavuconazole, Ravuconazole, Posaconazole, Voriconazole, Terconazole, Abafungin, Terbinafine, Amorolfine, Naftifine, Butenafine, Anidulafungin, Caspofungin, Micafungin, Benzoic acid, Ciclopirox, Tolnaftate, Undecylenic acid, 5-fluorocytosine, Griseofulvin, Haloprogin, and sodium bicarbonate.

Skin Penetration Enhancers

As used herein, "enhancement," "skin penetration enhancement," or "skin permeation enhancement," refer to an increase in the permeability of the skin to a drug, so as to increase the rate at which the drug permeates through the skin. Thus, "skin permeation enhancer," "skin penetration enhancer," or simply "enhancer" refers to an agent, or mixture of agents that achieves such permeation enhancement. Several compounds have been investigated for use as skin penetration enhancers. See, for example, U.S. Pat. Nos. 5,601, 839; 5,006,342; 4,973,468; 4,820,720; 4,006,218; 3,551,154; and 3,472,931.

A skin penetration enhancer as used herein means any compound that augments movement of active compound through the dermis, for instance, that allows a colloidal dispersion of lipid with a non-lipid so it can penetrate body tissues which are composed of lipids and water along with other dermis components. In one embodiment, the skin penetration enhancer is DMSO, however, any skin penetration enhancer suitable in and known in the art for transdermal formulations may be used, such a those that allow a colloidal dispersion of a lipid with a non lipid so it can penetrate body tissues which are composed of lipids and water along with other dermis components. In one embodiment, DMSO has been shown to be a preferred skin penetration enhancer and the invention provides a transdermal formulation or composition comprising a therapeutic compound, or pharmaceutically acceptable salts thereof and DMSO with or without nano colloidal silica.

In one embodiment, the composition may comprise one or more skin penetration enhancing agents for transdermal drug delivery. Non-limiting examples of skin penetration enhancing agents include $C_8$-$C_{22}$ fatty acids such as isostearic acid, octanoic acid, and oleic acid; $C_8$-$C_{22}$ fatty alcohols such as oleyl alcohol and lauryl alcohol; lower alkyl esters of $C_8$-$C_{22}$ fatty acids such as ethyl oleate, isopropyl myristate (IPM), butyl stearate, and methyl laurate; di(lower)alkyl esters of $C_6$-$C_{22}$ diacids such as diisopropyl adipate; monoglycerides of $C_8$-$C_{22}$ fatty acids such as glyceryl monolaurate; tetrahydrofurfuryl alcohol polyethylene glycol ether; polyethylene glycol, propylene glycol; 2-(2-ethoxyethoxy)ethanol (transcutol); diethylene glycol monomethyl ether; alkylaryl ethers of polyethylene oxide; polyethylene oxide monomethyl ethers; polyethylene oxide dimethyl ethers; dimethyl sulfoxide; glycerol; ethyl acetate; acetoacetic ester; N-alkylpyrrolidone; terpenes, dimethyl formamide (DMF), N,N-dimethylacetamide (DMA), diethylene glycol monoethyl or monomethyl ether with propylene glycol monolaurate and methyl laurate; glycerol monolaurate and ethanol, fatty acid esters or fatty alcohol ethers of $C_2$ to $C_4$ alkanediols, where each fatty acid/alcohol portion of the ester/ether is of about 8 to 22 carbon atoms.

The skin penetration enhancing agent is present in an amount sufficient to provide the desired physical properties and skin penetration profile for the composition. Illustratively, one or more pharmaceutically acceptable skin penetration enhancer can be present in a total amount by weight of the composition of about 0.1%, about 0.2%, about 0.3%, about 0.4%, about 0.5%, about 1.0%, about 1.5%, about 2.0%, about 2.5%, about 3.0%, about 3.5%, about 4.0%, about 4.5%, about 5.0%, about 5.5%, about 6.0%, about 6.5%, about 7.0%, about 7.5%, about 8.0%, about 8.5%, about 9.0%, about 9.5%, about 10.0%, about 10.5%, about 11.0%, about 11.5%, about 12.0%, about 12.5%, about 13.0%, about 13.5%, about 14.0%, about 14.5%, and or 15.0%. As a further illustration, one or more pharmaceutically acceptable skin penetration enhancer is present in a total amount by weight between about 0.1% and about 15%; between about 0.1% and about 10%; between about 0.5% and about 10%; or between about 3% and about 8%.

As a further illustration, one or more pharmaceutically acceptable skin penetration enhancer is present in a total amount by weight between about 1% and about 10%, between about 2% and about 10%, between about 3% and about 10%, between about 4% and about 10%, between about 5% and about 10%, between about 6% and about 10%, between about 7% and about 10%, between about 8% and about 10%, between about 9% and about 10%, between about 1% and about 9%, between about 2% and about 9%, between about 3% and about 9%, between about 4% and about 9%, between about 5% and about 9%, between about 6% and about 9%, between about 7% and about 9%, between about 8% and about 9%, between about 1% and about 8%, between about 2% and about 8%, between about 3% and about 8%, between about 4% and about 8%, between about 5% and about 8%, between about 6% and about 8%, between about 7% and about 8%, between about 1% and about 7%, between about 2% and about 7%, between about 3% and about 7%, between about 4% and about 7%, between about 5% and about 7%, between about 6% and about 7%, between about 1% and about 6%, between about 2% and about 6%, between about 3% and about 6%, between about 4% and about 6%, between about 5% and about 6%, between about 1% and about 5%, between about 2% and about 5%, between about 3% and about 5%, between about 4% and about 5%, between about 1% and about 4%, between about 2% and about 4%, between about 3% and about 4%, between about 1% and about 3%, between about 2% and about 3% and between about 1% and about 2%.

Thickening Agents

In one embodiment, the composition may comprise a thickening or gelling agent to increase the viscosity of the composition. None-limiting examples of thickening agents (aka gelling agents) which may be used herein include neutralized anionic polymers such as polyacrylic acid (CARBOPOL® by Noveon, Inc., Cleveland, Ohio), carboxypolymethylene, carboxymethylcellulose and the like, including derivatives of Carbopol® polymers, such as Carbopol® Ultrez 10, Carbopol® 940, Carbopol® 941, Carbopol® 954, Carbopol® 980, Carbopol® 981, Carbopol® ETD 2001, Carbopol® EZ-2 and Carbopol® EZ-3. Also suitable are other known polymeric thinking agents, such as Pemulen® polymeric emulsifiers, and Noveon® polycarbophils and Klucel®. Additional thickening agents, enhancers and adjuvants may generally be found in Remington's The Science and Practice of Pharmacy as well as the Handbook of Pharmaceutical Excipients, Arthur H. Kibbe ed. 2000. Thickening agents or gelling agents are present in an amount sufficient to provide the desired rheological properties of the composition. Illustratively, one or more pharmaceutically acceptable thickening agent or gelling agent are present in a total amount by weight of about 0.1%, about 0.25%, about 0.5%, about 0.75%, about 1%, about 1.25%, about 1.5%, about 1.75%, about 2.0%, about 2.25%, about 2.5%, about 2.75%, about 3.0%, about 3.25%, about 3.5%, about 3.75%, about 4.0%, about 4.25%, about 4.5%, about 4.75%, about 5.0%, about 5.25%, about 5.5%, about 5.75%, about 6.0%, about 6.25%, about 6.5%, about 6.75%, about 7.0%, about 7.25%, about 7.5%, about 7.75%, about 8.0%, about 8.25%, about 8.5%, about 8.75%, about 9.0%, about 9.25%, about 9.5%, about 9.75%, about 10%, about 11%, about 11.5%, about 12%, about 12.5%, about 13%, about 13.5%, about 14%, about 14.5% or about 15%. As a further illustration, one or more pharmaceutically acceptable thickening or gelling agent are present in a total amount by weight between about 0.1% and about 15%; about 0.5% and about 5%; or about 1% and about 3%.

Wetting Agents

Compositions described herein optionally comprise one or more pharmaceutically acceptable wetting agents as excipients. Non-limiting examples of surfactants that can be used as wetting agents in compositions of the disclosure include quaternary ammonium compounds, for example benzalkonium chloride, benzethonium chloride and cetylpyridinium chloride; dioctyl sodium sulfosuccinate; polyoxyethylene alkylphenyl ethers, for example nonoxynol 9, nonoxynol 10, and octoxynol 9; poloxamers (polyoxyethylene and polyoxypropylene block copolymers); polyoxyethylene fatty acid glycerides and oils, for example polyoxyethylene (8) caprylic/capric mono- and diglycerides (e.g., Labrasol™ of Gattefossé), polyoxyethylene (35) castor oil and polyoxyethylene (40) hydrogenated castor oil; polyoxyethylene alkyl ethers, for example polyoxyethylene (20) cetostearyl ether; polyoxyethylene fatty acid esters, for example polyoxyethylene (40) stearate; polyoxyethylene sorbitan esters, for example polysorbate 20 and polysorbate 80 (e.g., Tween™ 80 of ICI); propylene glycol fatty acid esters, for example propylene glycol laurate (e.g., Lauroglycol™ of Gattefossé); sodium lauryl sulfate, sodium laureth sulfate, fatty acids and salts thereof, for example oleic acid, sodium oleate and triethanolamine oleate; glyceryl fatty acid esters, for example glyceryl monostearate; sorbitan esters, for example sorbitan monolaurate, sorbitan monooleate, sorbitan monopalmitate and sorbitan monostearate; tyloxapol; and mixtures thereof. Such wetting agents, if present, constitute in total about 0.25% to about 15%, about 0.4% to about 10%, or about 0.5% to about 5%, of the total weight of the composition. Illustratively, one or more pharmaceutically acceptable wetting agents are present in a total amount by weight of about 0.25%, about 0.5%, about 0.75%, about 1%, about 1.25%, about 1.5%, about 1.75%, about 2.0%, about 2.25%, about 2.5%, about 2.75%, about 3.0%, about 3.25%, about 3.5%, about 3.75%, about 4.0%, about 4.25%, about 4.5%, about 4.75%, about 5.0%, about 5.25%, about 5.5%, about 5.75%, about 6.0%, about 6.25%, about 6.5%, about 6.75%, about 7.0%, about 7.25%, about 7.5%, about 7.75%, about 8.0%, about 8.25%, about 8.5%, about 8.75%, about 9.0%, about 9.25%, about 9.5%, about 9.75% or about 10%.

Lubricants

Compositions described herein optionally comprise one or more pharmaceutically acceptable lubricants (including antiadherents and/or glidants) as excipients. Suitable lubricants include, either individually or in combination, glyceryl behapate (e.g., Compritol™ 888); stearic acid and salts thereof, including magnesium (magnesium stearate), calcium and sodium stearates; hydrogenated vegetable oils (e.g., Sterotex™); colloidal silica; talc; waxes; boric acid; sodium benzoate; sodium acetate; sodium fumarate; sodium chloride; DL-leucine; PEG (e.g., Carbowax™ 4000 and Carbowax™ 6000); sodium oleate; sodium lauryl sulfate; sodium laureth sulfate and magnesium lauryl sulfate. Such lubricants, if present, constitute in total about 0.1% to about 10%, about 0.2% to about 8%, or about 0.25% to about 5%, of the total weight of the composition. Illustratively, one or more pharmaceutically acceptable lubricants are present in a total amount by weight of about 0.1%, about 0.2%, about 0.3%, about 0.4%, about 0.5%, about 0.6%, about 0.7%, about 0.8%, about 0.9%, about 1.0%, about 1.1%, about 1.2%, about 1.3%, about 1.4%, about 1.5%, about 1.6%, about 1.7%, about 1.8%, about 1.9%, about 2.0%, about 2.1%, about 2.2%, about 2.3%, about 2.4%, about 2.5%, about 2.6%, about 2.7%, about 2.8%, about 2.9%, about 3.0%, about 3.1%, about 3.2%, about 3.3%, about 3.4%, about 3.5%, about 3.6%, about 3.7%, about 3.8%, about 3.9%, about 4.0%, about 4.1%, about 4.2%, about 4.3%, about 4.4%, about 4.5%, about 4.6%, about 4.7%, about 4.8%, about 4.9%, about 5.0%, about 5.1%, about 5.2%, about 5.3%, about 5.4%, about 5.5%, about 5.6%, about 5.7%, about 5.8%, about 5.9%, about 6.0%, about 6.1%, about 6.2%, about 6.3%, about 6.4%, about 6.5%, about 6.6%, about 6.7%, about 6.8%, about 6.9%, about 7.0%, about 7.1%, about 7.2%, about 7.3%, about 7.4%, about 7.5%, about 7.6%, about 7.7%, about 7.8%, about 7.9%, about 8.0%, about 8.1%, about 8.2%, about 8.3%, about 8.4%, about 8.5%, about 8.6%, about 8.7%, about 8.8%, about 8.9%, about 9.0%, about 9.1%, about 9.2%, about 9.3%, about 9.4%, about 9.5%, about 9.6%, about 9.7%, about 9.8%, about 9.9% or about 10.0%.

Emollients

In another embodiment, the compositions described herein optionally comprise an emollient. Illustrative emollients include mineral oil, mixtures of mineral oil and lanolin alcohols, cetyl alcohol, cetostearyl alcohol, petrolatum, petrolatum and lanolin alcohols, cetyl esters wax, cholesterol, glycerin, glyceryl monostearate, isopropyl myristate (IPM), isopropyl palmitate, lecithin, allyl caproate, althea officinalis extract, arachidyl alcohol, argobase EUC, butylene glycol, dicaprylate/dicaprate, acacia, allantoin, carrageenan, cetyl dimethicone, cyclomethicone, diethyl succinate, dihydroabietyl behenate, dioctyl adipate, ethyl laurate, ethyl palmitate, ethyl stearate, isoamyl laurate, octanoate, PEG-75, lanolin, sorbitan laurate, walnut oil, wheat germ oil, super refined almond, super refined sesame, super refined soybean, octyl palmitate, caprylic/capric triglyceride and glyceryl cocoate.

An emollient, if present, is present in the compositions described herein in an amount of about 1% to about 30%, about 3% to about 25%, or about 5% to about 15%, by weight. Illustratively, one or more emollients are present in a total amount by weight of about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, or about 30%.

Water Soluble Celluloses

Celluloses are organic compounds with the general formula $(C_6H_{10}O_5)_n$, a polysaccharide consisting of a linear chain of several hundred to over ten thousands $\beta(1\rightarrow4)$ linked D-glucose units. Preferred celluloses include water-soluble celluloses, and modified water-soluble celluloses such as those known in the art and have properties similar to cellulose. Examples are methylcellulose of different viscosity, ethylcellulose, hydroxypropyl cellulose, hydroxymethylcellulose, and hydroxyethylcellulose, hydroxypropyl methylcellulose, Methocel® MC, and carboxymethylcellulose. These cellulose compounds, like cellulose itself, are not digestible by humans, and they are not toxic, and not allergenic.

Polysorbates

Polysorbates are a class of emulsifiers used in some pharmaceuticals and food preparation. Polysorbates are oily liquids derived from PEG-ylated sorbitan (a derivative of sorbitol) esterified with fatty acids. Polysorbates include but are not limited to polyoxyethylene (20) sorbitan monolaurate (polysorbate 20), polyoxyethylene (20) sorbitan monopalmitate (polysorbate 40), polyoxyethylene (20) sorbitan monostearate (polysorban 60), polyoxyethylene (20) sorbitan tristrearate (polysorban 65), and polyoxyethylene (20) sorbitan monooleate (polysorban 80).

Carbomers

Carbomer is a generic name for synthetic polymers of acrylic acid used as emulsion stabilizers or thickening agents in pharmaceuticals and cosmetic products. They may be homopolymers of acrylic acid, crosslinked with an allyl ether pentaerythritol, allyl ether of sucrose, or allyl ether of propylene. Carbomers include but are not limited to Carbopol® polymer 71G NF, Carbopol® polymer 971P NF, Carbopol® polymer 974P NF, carbopole polymer 980 NF, Carbopol® polymer 981 NF, Carbopol® polymer 5984 EP and Carbopol® polymer Ultrez 10 NF.

Polyethylene Glycol (PEG)

PEG refers to an oligomer or polymer of ethylene oxide and are prepared by polymerization of ethylene oxide and are commercially available over a wide range of molecular weights from 300 g/mol to 10,000,000 g/mol. The preferred PEG to be used in the present invention are liquid PEGs including but not limited to PEG 200, PEG 200E, PEG 300, PEG 300E, PEG 400, PEG 400E, PEG 600 and PEG 600E. The present invention will be more readily understood by referring to the following examples which are given to illustrate the invention rather than to limit its scope.

Antiseptic Agents

The composition of the present invention may also be prepared by the addition of an antiseptic agent in order to keep the composition sterile and disinfect the surfaces onto which it is applied during use. The preferred antiseptic agents include but are not limited to chlorhexidine gluconate, glucono delta-lactone, a paraben compound, benzoic acid, imidazolidinyl urea, a quaternary ammonium compound, methyl hydroxybenzoate, propyl hydroxybenzoate, chlorocresol, benzalkonium chloride and Octenidine dihydrochloride.

Preservative Agent

Furthermore, in order to stabilize and keep the composition for extended periods of time, preservative agents may be added to the composition. The preferred preservative agents include but are not limited to EDTA, EGTA, hydroxytoluene butoxide, hydroxyanisol butoxide, sodium hydroxide, calcium propionate, sodium nitrate, sodium nitrite, sulfur dioxide, sodium bisulfite, benzoic acid, caprylyl glycol, Diazolidinyl urea, Phenoxyethanol, Dehydroacetic acid, Iodopropynylbutylcarbamate, Sorbic acid, Isopropyl-paraben, Isobutyl-paraben, Butyl-paraben, and potassium hydrogen sulfite.

Use of the Composition

According to one embodiment, the method and the compositions of the present invention are used for improving vascular circulation, and prophylaxis or treatment of a condition associated with impaired blood circulation in a patient by treating transdermally the patient with a composition according to an embodiment of the present invention to treat and/or alleviate the symptoms of peripheral vascular disease.

Preferably, the method and the compositions are for prophylaxis or treatment of Peripheral vascular disease (PVD), commonly referred to as peripheral arterial disease (PAD) and rarely referred to as peripheral artery occlusive disease (PAOD), refers to the obstruction of large arteries not within the coronary or aortic arch vasculature. PVD can result from atherosclerosis, inflammatory processes leading to stenosis, an embolism, or thrombus formation. It causes either acute or chronic ischemia (lack of blood supply). Often PAD is a term used to refer to atheresclortic blockages found in the lower extremity. PVD also includes a subset of diseases classified as microvascular diseases resulting from episodal narrowing of the arteries (Raynaud's phenomenon), or widening thereof (erythromelalgia), i.e. vascular spasms.

Typical symptoms of PVD include claudication, characterized by pain, weakness, numbness, or cramping in muscles of the limbs due to decreased blood flow. The affected limb(s) display sores, wounds, or ulcers that heal slowly or not at all, and they also have a noticeable change in color (blueness or paleness) or temperature (coolness) when compared to the other limbs. Furthermore, there is diminished hair and nail growth on affected limb and digits.

PVD has a number of causations, which include tobacco use, which in any form is the single most important modifiable cause of PVD internationally. Smokers have up to a tenfold increase in relative risk for PVD in a dose-related effect. Exposure to second-hand smoke from environmental exposure has also been shown to promote changes in blood vessel lining (endothelium) which is a precursor to atherosclerosis.

Diabetes mellitus is also associated with PVD as individuals with diabetes mellitus have between two and four times increased risk of PVD by causing endothelial and smooth muscle cell dysfunction in peripheral arteries. Diabetics account for up to 70% of nontraumatic amputations performed, and a known diabetic who smokes runs an approximately 30% risk of amputation within 5 years.

The elevation of total cholesterol, LDL cholesterol, and triglyceride levels (collectively referred to as dyslipidemia) each have been correlated with accelerated PVD. Correction of dyslipidemia by diet and/or medication is associated with a major improvement in short-term rates of heart attack and stroke.

Elevated blood pressure (hypertension) is correlated with an increase in the risk of developing PVD, as well as in associated coronary and cerebrovascular events (heart attack and stroke). Other risk factors which are being studied include levels of various inflammatory mediators such as C-reactive protein, homocysteine, and an over active sex life may increase risk of contracting PVD. Risk of PVD also increases if the patient is: over the age of 50, African American, male, obese, or has a personal history of vascular disease, heart attack, or stroke.

In embodiments, the composition of the present invention is used to topically treat the affected limb or area in order to increase vasodilatation of the blood vessels and improve blood flow therein.

According to another embodiment, the compositions of the present invention are also used for treating ulcers in a patient. The patient may be treated topically with a gel or a cream according to the present invention, and/or treating the patient transdermally with the composition according to an embodiment of the present invention to treat the ulcer.

Skin ulcers appear as open craters, often round, with layers of skin that have eroded. The skin around the ulcer may be red, swollen and tender. Patients may feel pain on the skin around the ulcer, and fluid may ooze from the ulcer. In some cases, ulcers can bleed and, rarely, patients experience fever. Ulcers sometimes seem not to heal; healing, if it does occur, tends to be slow. Ulcers that heal within 12 weeks are usually classified as acute, and longer-lasting ones as chronic.

Chronic ulcers may be painful. Most patients complain of constant pain at night and during the day. Chronic ulcers symptoms usually include increasing pain, friable granulation tissue, and foul odour and wound breakdown instead of healing. Symptoms tend to worsen once the wound has become infected. Venous skin ulcers that may appear on the lower leg, above the calf or on the lower ankle usually cause achy and swollen legs. If these ulcers become infected they may develop an unpleasant odour, increased tenderness and redness. Before the ulcer establishes definitively, there may be a dark red or purple skin over the affected area as well as a thickening, drying and itchy skin.

Although skin ulcers do not seem of great concern at a first glance, they are worrying conditions especially in people suffering from diabetes, as they are at risk of developing diabetic neuropathy. Diabetic foot ulcer is one of the major complications of Diabetes mellitus. It occurs in 15% of all patients with diabetes and precedes 84% of all lower leg amputations. Diabetic foot ulcers, occur as a result of various factors. Such factors include mechanical changes in conformation of the bony architecture of the foot, peripheral neuropathy, and atherosclerotic peripheral arterial disease, all of which occur with higher frequency and intensity in the diabetic population.

Ulcers may also appear on the cheeks, soft palate, the tongue, on the inside of the lower lip, and sometimes on other mucous membranes. These ulcers usually last from 7 to 14 days and can be painful.

The wounds from which ulcers arise can be caused by a wide variety of factors, such as heat, cold, inflammation and prolonged pressure on the tissue, but the main cause is impaired blood circulation.

Ulcer include a skin ulcer, a decubitus ulcer, a mouth ulcer, a diabetic foot ulcer, a venous insufficiency ulcer, a venous ulcer, an arterial insufficiency ulcer, a neuropathic ulcer, a genital ulcer.

Other condition associated with impaired blood circulation include sores, and wounds, peripheral vascular disease, atherosclerosis, Raynaud's phenomenon, and gangrene.

While preferred embodiments have been described above and illustrated in the accompanying drawings, it will be evident to those skilled in the art that modifications may be made without departing from this disclosure. Such modifications are considered as possible variants comprised in the scope of the disclosure.

The invention claimed is:

1. A topical composition comprising:
an effective amount of a compound selected from the group consisting of (2-nitrooxy)-2-ethylamino-3-methylbutanoate

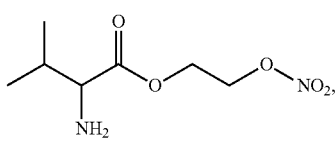

valine butylene glycol nitrate

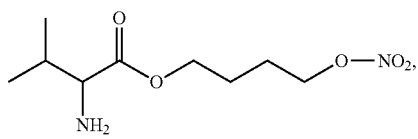 [SMILES: CC(C)C(N)C(=O)OCCCCO[N+](=O)[O-]]

2'-nitrooxyethyl 2-amino-pentanoate

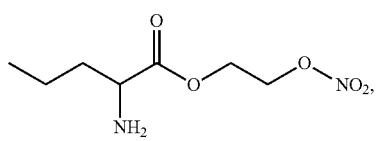

and 4'-nitrooxybutyl 2-amino-pentanoate

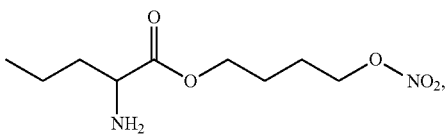 [SMILES: CCCC(N)C(=O)OCCCCO[N+](=O)[O-]]

or any pharmaceutically acceptable salts thereof; and
at least one topical antimicrobial,
in association with a pharmaceutically acceptable topical carrier.

2. The composition as claimed in claim 1, wherein said topical antimicrobial is at least one of a topical antibiotic chosen from amikacin, gentamicin, kanamycin, neomycin, netilmicin, tobramycin, paromomycin, geldanamycin, herbimycin, loracarbef, ertapenem, doripenem, imipenem/cilastatin, meropenem, cefadroxil, cefazolin, cefalotin, cefalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, ceftobiprole, teicoplanin, vancomycin, telavancin, clindamycin, lincomycin, azithromycin, clarithromycin, dirithromycin, erythromycin, roxithromycin, troleandomycin, telithromycin, spectinomycin, aztreonam, furazolidone, nitrofurantoin, amoxicillin, ampicillin, azlocillin, carbenicillin, cloxacillin, dicloxacillin, flucloxacillin, mezlocillin, methicillin, nafcillin, oxacillin, penicillin g, penicillin v, piperacillin, temocillin, ticarcillin, amoxicillin and clavulanate, ampicillin and sulbactam, piperacillin and tazobactam, ticarcillin and clavulanate, bacitracin, colistin, polymyxin b, ciprofloxacin, enoxacin, gatifloxacin, levofloxacin, lomefloxacin, moxifloxacin, nalidixic acid, norfloxacin, ofloxacin, trovafloxacin, grepafloxacin, sparfloxacin, temafloxacin, mafenide, sulfonamidochrysoidine, sulfacetamide, sulfadiazine, silver sulfadiazine, sulfamethizole, sulfamethoxazole, sulfanilimide, sulfasalazine, sulfisoxazole, trimethoprim, trimethoprim-sulfamethoxazole, demeclocycline, doxycycline, minocycline, oxytetracycline, tetracycline, clofazimine, dapsone, capreomycin, cycloserine, ethambutol, ethionamide, isoniazid, pyrazinamide, rifampicin, rifabutin, rifapentine, streptomycin, arsphenamine, chloramphenicol, fosfomycin, fusidic acid, linezolid, metronidazole, mupirocin, platensimycin, quinupristin/dalfopristin, rifaximin, thiamphenicol, and tinidazole,
a topical antifungal chosen from natamycin, rimocidin, filipin, nystatin, amphotericin b, candicin, hamycin, miconazole, ketoconazole, clotrimazole, econazole, bifonazole, butoconazole, fenticonazole, isoconazole, oxiconazole, sertaconazole, sulconazole, tioconazole, fluconazole, itraconazole, isavuconazole, ravuconazole, posaconazole, voriconazole, terconazole, abafungin, terbinafine, amorolfine, naftifine, butenafine, anidulafungin, caspofungin, micafungin, benzoic acid, ciclopirox, tolnaftate, undecylenic acid, 5-fluorocytosine, griseofulvin, haloprogin, and sodium bicarbonate,
and combinations thereof.

3. The composition of claim 1, further comprising a skin penetration enhancer chosen from a $C_8$-$C_{22}$ fatty acid, a $C_8$-$C_{22}$ fatty alcohol, a lower alkyl ester of a $C_8$-$C_{22}$ fatty acid, a di(lower)alkyl ester of $C_6$-$C_{22}$ diacid, a monoglyceride of $C_8$-$C_{22}$ fatty acid, tetrahydrofurfuryl alcohol polyethylene glycol ether, polyethylene glycol, propylene glycol, 2-(2-ethoxyethoxy)ethanol (transcutol), diethylene glycol monomethyl ether, diethylene glycol monoethyl ether, an alkylaryl ether of polyethylene oxide, a polyethylene oxide monomethyl ether, a polyethylene oxide dimethyl ether; dimethyl sulfoxide (DMSO), glycerol, ethyl acetate, acetoacetic ester, N-alkylpyrrolidone, a terpenes, dimethyl formamide (DMF), N,N-dimethylacetamide (DMA), methyl laurate, glycerol monolaurate, a fatty acid ester of a $C_2$ to $C_4$ alkanediol having a fatty acid portion of said ester from about 8 to 22 carbon atoms, a fatty alcohol ether of a $C_2$ to $C_4$ alkanediols having a fatty acid portion of said ether from about 8 to 22 carbon atoms, triglycerides of coconut oil, isopropyl palmitate, isopropyl myristate, laurocapram, and combinations thereof.

\* \* \* \* \*